US011179381B2

(12) United States Patent
Pellikaan et al.

(10) Patent No.: US 11,179,381 B2
(45) Date of Patent: Nov. 23, 2021

(54) INTRANASAL ADMINISTRATION OF PHYSIOLOGICALLY ACTIVE SUBSTANCES

(71) Applicant: DUTCH RENEWABLE ENERGY B.V., Muiden (NL)

(72) Inventors: Hubert Clemens Pellikaan, Utrecht (NL); Rolf Lourens Visser, Muiden (NL)

(73) Assignee: DUTCH RENEWABLE ENERGY B.V., Muiden (NL)

( * ) Notice: Subject to any disclaimer, the term of this patent is extended or adjusted under 35 U.S.C. 154(b) by 0 days.

(21) Appl. No.: 16/557,816

(22) Filed: Aug. 30, 2019

(65) Prior Publication Data
US 2019/0381027 A1 Dec. 19, 2019

Related U.S. Application Data

(63) Continuation of application No. PCT/EP2018/054777, filed on Feb. 27, 2018.

(30) Foreign Application Priority Data

Mar. 2, 2017 (EP) ..................... 17158850

(51) Int. Cl.
| | | |
|---|---|---|
| A61K 31/465 | (2006.01) | |
| A61K 9/00 | (2006.01) | |
| A61K 31/197 | (2006.01) | |
| A61K 31/4188 | (2006.01) | |
| A61K 31/51 | (2006.01) | |
| A61K 31/519 | (2006.01) | |
| A61K 31/525 | (2006.01) | |
| A61K 31/675 | (2006.01) | |
| A61K 31/714 | (2006.01) | |
| A61K 38/18 | (2006.01) | |
| A61K 31/522 | (2006.01) | |

(52) U.S. Cl.
CPC ............ *A61K 31/465* (2013.01); *A61K 9/008* (2013.01); *A61K 9/0043* (2013.01); *A61K 31/197* (2013.01); *A61K 31/4188* (2013.01); *A61K 31/51* (2013.01); *A61K 31/519* (2013.01); *A61K 31/522* (2013.01); *A61K 31/525* (2013.01); *A61K 31/675* (2013.01); *A61K 31/714* (2013.01); *A61K 38/1816* (2013.01)

(58) Field of Classification Search
CPC .. A61K 31/465; A61K 31/714; A61K 31/197; A61K 31/4188; A61K 31/51; A61K 31/519; A61K 31/525; A61K 31/675; A61K 31/4415; A61K 9/0043; A61K 9/008; A61K 9/08
See application file for complete search history.

(56) References Cited

U.S. PATENT DOCUMENTS

| | | | | |
|---|---|---|---|---|
| 2,823,167 | A * | 2/1958 | Newmark | ............... A61K 31/00 514/52 |
| 2010/0210580 | A1 * | 8/2010 | Feller | ................... A61K 47/186 514/52 |
| 2014/0072588 | A1 | 3/2014 | Illum et al. | |
| 2016/0022726 | A1 | 1/2016 | Feller et al. | |

FOREIGN PATENT DOCUMENTS

| | | |
|---|---|---|
| DE | 4430154 A1 | 5/1995 |
| EP | 0967214 A1 | 12/1999 |

OTHER PUBLICATIONS

Noh et al., J. Kor. Pharm. Sci., 2004, 34(2), pp. 131-138. (Year: 2004).*
Shukla, T., et al., "Role of Hydrotropic Salt Solutions in Pharmaceutical Research: Past Present and Future", International Journal of Pharmacy and Pharmaceutical Sciences, 2014, 6(4):3-6.
International Preliminary Report on Patentability for PCT/EP2018/054777, dated Feb. 14, 2019, 15 pages.

* cited by examiner

*Primary Examiner* — Jonathan S Lau
(74) *Attorney, Agent, or Firm* — Foley & Lardner LLP; Gilberto M. Villacorta

(57) ABSTRACT

The present invention relates to a method for administering water soluble physiologically active substances, said method comprising intranasally administering to a subject an aqueous composition comprising 0.001-25 wt. % of one or more fully dissolved physiologically active substances, the physiologically active substances having a water solubility in demineralized water of at least 15 mg/mL at 20° C. of, 0.01-10 wt. % nicotinamide, and at least 60 wt. % water. The invention also relates to a kit comprising said composition and to the use of nicotinamide as an enhancer of intranasal absorption of a physiologically active substance from an aqueous solution, wherein the aqueous solution further comprises 0.01-10 wt. % nicotinamide.

24 Claims, No Drawings

INTRANASAL ADMINISTRATION OF PHYSIOLOGICALLY ACTIVE SUBSTANCES

CROSS-REFERENCE TO RELATED PATENT APPLICATIONS

This application is a continuation of International Application No. PCT/EP2018/054777 filed Feb. 27, 2018, which claims priority to European Application No. 17158850.2 filed Mar. 2, 2017. The specification, claims and abstract of the prior applications are incorporated herein by reference in their entirety.

FIELD

The present invention relates to the intranasal administration of physiologically active substances, more particularly to the intranasal administration of an aqueous composition containing a fully dissolved physiologically active substance and an intranasal absorption enhancer.

BACKGROUND

Intranasal administration offers a variety of attractive options for local and systemic delivery of water soluble physiologically active substances. The nature of the nasal mucosa provides a series of unique attributes, all of which may help to maximize the patient's safety, convenience and compliance. Administration of physiologically active agents via nasal mucosa, offers advantages over other routes of administration, for example oral administration as the active substance is transported directly into the systemic circulation and therefore avoids first pass metabolism. Additionally, active agents can be directly absorbed into the CNS after nasal administration by crossing the olfactory mucosa or being transported via the trigeminal nerve system in the nasal cavity known as the nose to brain pathway.

Even though the nasal mucosa within the nasal cavity provide an ideal absorption area, the natural permeation barrier and the efficient cleansing mechanism confine the total amount of active substance that can be absorbed. Among the major disadvantages of the nasal route are the limited application volume (25-250 μL), the difficulty of high molecular weight drugs (>1,000 Da) to pass through the nasal mucosa, the presence of pathological conditions, mucocilliary drug clearance, enzymatic barriers and irritation of the nasal mucosa. Efforts have been made to improve absorption of water soluble physiologically active substances when administered by nasal administration.

EP-A 0 967 214 describes an intranasal pharmaceutical formulation for the treatment of male erectile dysfunction or female sexual disorders which comprises sildenafil mesylate, together with a pharmaceutically acceptable diluent or carrier in a form adapted for intranasal administration. Example 2 describes an intranasal solution formulation containing sildenafil mesylate, nicotinamide and water.

DE-A 44 30 154 describes an aqueous antidepressive composition comprising 100 mL distilled water; 0.1 gram nicotinic acid; 1 gram nicotinamide; and 10 grams sodium ascorbate. This composition was applied to patients suffering from depression by dripping the aqueous composition into the eye corner (0.5-0.7 mL) or by applying the composition to the nasal mucosa (1-1.2 mL).

US 2014/0072588 discloses a composition comprising insulin and Solutol®HS15 in varying concentrations from 1 to 40% w/v. Solutol® is a hydroxy fatty acid ester of polyethylene glycol. US 2014/0072588 teaches that when a hydroxy fatty acid ester of polyethylene glycol is used in combination with a therapeutic agent, the therapeutic agent is absorbed across the mucosal surface to a much higher degree than if the hydroxy fatty acid ester of polyethylene glycol were not present in the formulation.

US 2016 022726 A1 discloses a composition for nasal administration of vitamin B12, specifically an aqueous solution comprising about 0.02% w/w to about 1% w/w of a cobalamin compound and a pharmaceutically acceptable buffer, wherein the composition has a pH of about 4 to about 6.5 and wherein the cobalamin compounds is cyanocobalamin or a hydroxocobalamin. Furthermore, US 2016 022726 A1 discloses the following enhancers of nasal adsorption: polyoxyethylene derivatives of fatty acids, partial esters of sorbitol anhydrides, sodium lauryl sulfate, sodium salicylate, oleic acid, lecithin, dehydrated alcohol, Tween (e.g., Tween 20, Tween 40, Tween 60, Tween 80 and the like), Span (e.g., Span 20, Span 40, Span 80 and the like), polyoxyl 40 stearate, polyoxy ethylene 50 stearate, edetate disodium, propylene glycol, glycerol monooleate, fusieates, bile salts, octoxynol and combinations thereof. The effectiveness of these absorption enhancers is often disappointing and some of these enhancers produce undesirable side effects such as sensitisation and irritation.

There remains a need for intranasal formulations of physiologically active substances that are safe to use and that achieve effective intranasal absorption of the physiologically active substance.

SUMMARY

The inventors have unexpectedly discovered that the intranasal absorption of water-soluble physiologically active substances from aqueous solutions can be enhanced significantly by including nicotinamide in a suitable concentration.

Thus, one aspect of the present invention relates to a non-therapeutic method for administering water soluble physiologically active substances, said method comprising intranasally administering to a subject an aqueous composition comprising:
  0.001-25 wt. % of one or more fully dissolved physiologically active substances, including at least 0.001 wt. % of one or more vitamins and/or at least 0.001 wt. % of caffeine, the physiologically active substances having a water solubility in demineralized water of at least 15 mg/mL at 20° C. of, wherein the aqueous composition does not comprise both niacin and ascorbic acid;
  0.01-10 wt. % nicotinamide; and
  at least 60 wt. % water.

Another aspect of the invention relates to an aqueous composition for use in the prophylactic or therapeutic treatment of a disorder, the treatment comprising intranasally administering of an aqueous composition comprising:
  0.001-25 wt. % of one or more fully dissolved physiologically active substances, the physiologically active substances having a water solubility in demineralized water of at least 15 mg/mL at 20° C.; wherein the one or more physiologically active substances are present in the aqueous composition in a concentration that is below their water-solubility limit at 20° C.;
  0.01-10 wt. % nicotinamide; and
  at least 60 wt. % water;
wherein the aqueous composition is intranasally administered as a spray or an aerosol in a dose of 0.01 to 0.3 ml to provide the one or more physiologically active substances in a dose of 10-10,000 μg.

Examples of water soluble physiologically active substance whose intranasal absorption can be enhanced by applying them in an aqueous formulation according to the present invention include water soluble vitamins, peptides, proteins and alkaloids such as caffeine.

Without wishing to be bound by theory, it is believed that increase in absorption across nasal mucosa is due to nicotinamide improving mucosal membrane permeability.

Given the improved absorption of the physiologically active substances in the present invention, lower doses of the physiologically active substance need be administered. This means that the concentration of the physiologically active substance in the formulation can be reduced and/or that the dose of administration can be reduced.

The present invention also provides the use of nicotinamide as an enhancer of intranasal absorption of a physiologically active substance from an aqueous solution, wherein the aqueous solution further comprises 0.01-10 wt. % nicotinamide.

Furthermore, the invention relates to a kit comprising:
a container comprising an aqueous composition as defined above; and
a nasal applicator device for intranasal administration in fluid communication with the aqueous composition.

DETAILED DESCRIPTION

In a first aspect, the present invention relates to a non-therapeutic method for administering water soluble physiologically active substances, said method comprising intranasally administering to a subject an aqueous composition comprising:
0.001-25 wt. % of one or more fully dissolved physiologically active substances, including at least 0.001 wt. % of one or more vitamins and/or at least 0.001 wt. % of caffeine, the physiologically active substances having a water solubility in demineralized water of at least 15 mg/mL at 20° C., wherein the aqueous composition does not comprise both niacin and ascorbic acid (including salts of these acids);
0.01-10 wt. % nicotinamide; and
at least 60 wt. % water.

The term "nicotinamide" as used herein refers to pyridine-3-carboxamide, also known as niacinamide, as well as physiologically acceptable (dissociated) salts thereof. Nicotinamide is represented by structural formula I:

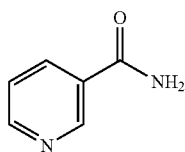

Formula I

The term "vitamin" as used herein means an organic compound that is a vital nutrient that humans require in limited amounts. The term "vitamin" does not include essential fatty acids or essential amino acids.

The term "peptide" as used herein means a chemical compound derived from two to hundred amino acid molecules (the same or different) by formation of a covalent bond from the carbonyl carbon of one to the nitrogen atom of another with formal loss of water.

The term "protein" as used herein means a naturally occurring or (semi-)synthetic polypeptide derived from more than hundred amino carboxylic acid molecules.

The term "caffeine" as used herein refers to 1,3,7-Trimethylxanthine as well as physiologically acceptable (dissociated) salts thereof.

Suitable physiologically acceptable salts may be organic or inorganic. Suitable organic physiologically acceptable salts include, but are not limited to, citrate and formate. Suitable inorganic physiologically acceptable salts include, but are not limited to, chloride and iodide.

The water soluble physiologically active substance that is employed in accordance with the present invention preferably has a solubility in demineralized water of at least 15 mg/mL at 20° C., preferably at least 20 mg/mL at 20° C. more preferably at least 33 mg/mL, even more preferably at least 66 mg/mL at 20° C. Typically, the water solubility of water soluble physiologically active in demineralized water at 20° C. does not exceed 100 mg/mL.

Preferably, the water soluble physiologically active substance has a log P of less than 0.5, more preferably less than 0, even more preferably less than −0.5. Log P corresponds to the octanol/water partition coefficient and represents the lipophilicity of a substance.

As explained herein before, the nicotinamide in the aqueous composition enhances intranasal absorption of the physiologically active substance. In other words, preferably the nicotinamide is not employed as a solubility enhancer. Accordingly, in a particularly preferred embodiment, the physiologically active substance is present in the aqueous composition in a concentration that is below its water-solubility at 20° C. Even more preferably, the physiologically active substance it present in a concentration that is below 90% more preferably below 80% of its water-solubility at 20° C.

In another preferred embodiment, the aqueous composition contains 0.001-20 wt. %, more preferably 0.005-15 wt. %, even more preferably 0.001-10 wt. % and most preferably 0.001-5 wt. % of the one or more physiologically active substances.

Nicotinamide is preferably present in the aqueous composition in a concentration of 0.05-8 wt. %, more preferably of 0.1-7 wt. %, even more preferably of 0.5-6 wt. % and most preferably of 1-5 wt. %.

In one preferred embodiment, the water soluble physiologically active substance is a vitamin selected from the group consisting of ascorbic acid (vitamin C), thiamine (vitamin B1), riboflavin (vitamin B2), niacin (vitamin B3), pantothenic acid (vitamin B5), pyridoxine (vitamin B6), biotin (vitamin B7), folic acid (vitamin B9) cyanocobalamin, hydroxocobalamin, methylcobalamin (vitamin B12) and salts and mixtures thereof. In a preferred embodiment the vitamin employed is a vitamin B12 component selected from the group consisting of cyanocobalamin, hydroxocobalamin and methylcobalamin. In another preferred embodiment, the vitamin is pyridoxine (vitamin B6). In yet another preferred embodiment, the vitamin is folic acid (vitamin B9).

In yet another preferred embodiment, the water soluble physiologically active substance is 1,3-7-trimethylxanthine (caffeine).

Preferably, the aqueous composition has a pH in the range of 4.5 to 6.5, more preferably in the range of 5.0 and 6.2, even more preferably in the range of 5.5 and 6.0.

In a preferred embodiment, the aqueous composition comprises no more than 1 wt. %, preferably no more than 0.5 wt % of surfactants, polymeric and polyhydroxyl excipients.

It is therefore now possible to formulate compositions of water soluble physiologically active substances for nasal administration that are essentially free from surfactants, polymeric or polyhydroxyl excipients. These excipients that have previously been used as absorption enhancers but are known to have undesirable side effects. Furthermore, as the bioavailability of the water soluble physiologically active substances in improved in the method of the invention, lower concentrations of water soluble physiologically active substances can be used. Advantages of this include improvements in the osmolarity of the composition, so that isotonic compositions can be prepared which are less painful to the subject than high concentrations of water soluble physiologically active substances.

The aqueous composition preferably has an osmolarity of between 200 and 500 mOsm/L, more preferably between 260 and 380 mOsm/L.

The present method preferably comprises intranasally administering the composition in a dose of 0.0001 to 0.3 ml, more preferably of 0.001 to 0.2 ml, most preferably of 0.01 to 0.1 ml, even more preferably 0.05-0.2 ml. The composition is preferably administered as a spray or aerosol.

The term "aerosol" means a mist of liquid particles. The dispensing system for such a formulation may be a can or bottle that contains a liquid pressurized by compressed, propellant gas.

The term "spray" means a fine dispersion of liquid particles that may be produced by a hand-operated pump and forced through an atomizer nozzle.

A typical nasal spray formulation consists of a bottle containing an aqueous composition of a physiologically active substance. Pump actuation by the subject delivers the physiologically active substance into the nasal cavity.

In a preferred embodiment, the one or more physiologically active substances are administered to the subject in a does that is between 10 and 10,000 µg, preferably between 50 and 1000 µg, even more preferably between 100 and 500 µg.

In a second aspect, the present invention relates to a kit comprising:
  at least one container comprising an aqueous composition comprising:
    0.001-25 wt. % of one or more fully dissolved physiologically active substances, including at least 0.001 wt. % of one or more vitamins and/or at least 0.001 wt. % of caffeine, the physiologically active substances having a water solubility in demineralized water of at least 15 mg/mL at 20° C.;
    0.01-10 wt. % nicotinamide;
    at least 60 wt. % water;
  a nasal applicator device for intranasal administration in fluid communication with the aqueous composition.

The kit provides a simple, user friendly way to administer the composition as defined herein.

In a preferred embodiment, the nasal applicator device is connected to the container comprising the composition. The nasal applicator device is preferably adapted to provide a metered dose of the composition to the nasal cavity of a subject in the form of a spray or an aerosol.

In another preferred embodiment, the nasal applicator device is detachably connected to the container comprising the composition. The container can be removed from the nasal applicator device by, for example, unscrewing or unclipping. In this way, when the container is empty, a user may attach the nasal applicator device to a new, full container, thus avoid unnecessary wastage of the nasal applicator device.

The container may be a vial, ampule, bottle or other suitable receptacle for containing the composition. The container may have receiving means adapted to receive the nasal applicator device so that when the container is suitably connected to the nasal applicator device, the composition can be administered intranasally to a subject. The container may comprise means for opening the container such as a screw cap, snap line in the case of ampules, puncture seal or other such means for opening the container so that the composition can be transferred from the container to the nasal applicator device. In this way, the nasal applicator device can be refilled allowing the user to reuse the device rather than throwing the nasal applicator away after a single use.

A third aspect of the present invention relates to an aqueous composition for use in the prophylactic or therapeutic treatment of a disorder, the treatment comprising intranasally administering of an aqueous composition comprising:
  0.001-25 wt. % of one or more fully dissolved physiologically active substances, the physiologically active substances having a water solubility in demineralized water of at least 15 mg/mL at 20° C.; wherein the one or more physiologically active substances are present in the aqueous composition in a concentration that is below their water-solubility limit at 20° C.;
  0.01-10 wt. % nicotinamide; and
  at least 60 wt. % water;
wherein the aqueous composition is intranasally administered as a spray or an aerosol in a dose of 0.01 to 0.3 ml to provide the one or more physiologically active substances in a dose of 10-10,000 µg.

In one preferred embodiment, the water soluble physiologically active substance that is employed in this treatment is a vitamin selected from the group consisting of ascorbic acid (vitamin C), thiamine (vitamin B1), riboflavin (vitamin B2), niacin (vitamin B3), pantothenic acid (vitamin B5), pyridoxine (vitamin B6), biotin (vitamin B7), folic acid (vitamin B9) cyanocobalamin, hydroxocobalamin, methylcobalamin (vitamin B12) and salts and mixtures thereof. In a preferred embodiment the vitamin employed is a vitamin B12 component selected from the group consisting of cyanocobalamin, hydroxocobalamin and methylcobalamin. In another preferred embodiment, the vitamin is pyridoxine (vitamin B6). In yet another preferred embodiment, the vitamin is folic acid (vitamin B9). In a preferred embodiment, the aqueous composition does not comprise both niacin and ascorbic acid.

In a further preferred embodiment, the water soluble physiologically active substance that is employed in the treatment is an amphetamine or derivative thereof. In a particularly preferred embodiment, amphetamine or derivative thereof is methylphenidate.

In a further preferred embodiment, the water soluble physiologically active substance that is employed in the treatment is a peptide selected from the group consisting of calcitonin, insulin, oxytocin, vasopressin, epidermal growth factor, somatostatin, glucagon GLP-1 related compounds, angiotensin, gastrin tetragastrin, pentagastrin, bradykinin, bacitracins, polymixins, colistins, tyrocidin, gramicidins, melanocortins, and derivatives thereof. Preferably, the peptide is calcitonin. Derivatives of the aforementioned peptides include analogues of the said peptides in which at least one amino acid in the peptide sequence has been modified, replaced or deleted. Modified peptides include, for example, conjugation at least one amino acid to polyalkene oxide moieties or polyhydroxyl moieties. Alternatively the native amino acid sequence may altered by replacing one or more native amino acids by a non-native amino acid or synthetic amino acid. Truncated peptide derivatives (where at least one amino acid has been deleted) may be produced by synthesis of 'fragments' corresponding to different lengths of the naturally occurring peptide sequence.

In yet another preferred embodiment, the water soluble physiologically active substance that is employed in the treatment is a protein selected from the group consisting of erythropoietin, adrenocorticotropin platelet-derived growth factor prolactin, luteinising hormone releasing hormone, growth hormone releasing hormone, secretin, tumor necrosis factor, nerve growth factor, granulocyte colony stimulating factor, granulocyte macrophage colony stimulating factor, immunoglobulins and renin. In a particularly preferred embodiment, the protein is erythropoietin.

It has been found that the use of nicotinamide as an absorption enhancer is not limited to low molecular weight substances, but nicotinamide also enhances the absorption of active substances having a high molecular weight of e.g. more than 1000 Da. The water soluble physiologically active substance preferably has a molecular weight of between 100 and 100,000 Da.

In a preferred embodiment, the water soluble physiologically active substance that is employed in the treatment is a vitamin, having a molecular weight of between 100 and 1500 Da.

In another preferred embodiment, the water soluble physiologically active substance that is employed in the treatment is a peptide having a molecular weight of between 500 and 10,000 Da, preferably between 1000 and 7000 Da, even more preferably between 1000 and 500 Da.

In another preferred embodiment, the water soluble physiologically active substance that is employed in the treatment is a protein, the molecular weight is preferably between 10,000 and 100,000 Da, more preferably between 10,000 and 75,000 Da, even more preferably between 10,000 and 50,000 Da.

The use of the aqueous composition in the aforementioned prophylactic or therapeutic treatment preferably comprises intranasal administration in way as described herein before in relation to the non-therapeutic method for administering water soluble physiologically active substances.

In a preferred embodiment, the disorder is selected from the group consisting of vitamin deficiency, heart disease, endocrine disorders, cancer, asthma, respiratory disorders, and bone disorders.

In a preferred embodiment, the disorder is a water soluble vitamin deficiency and the water soluble physiologically active substance employed in the treatment is a vitamin selected from the group consisting of ascorbic acid (vitamin C), thiamine (vitamin B1), riboflavin (vitamin B2), niacin (vitamin B3), pantothenic acid (vitamin B5), pyridoxine (vitamin B6), biotin (vitamin B7), folic acid (vitamin B9) cyanocobalamin, hydroxocobalamin, methylcobalamin (vitamin B12) and salts and mixtures thereof, on the proviso that the mixture does not comprise both niacin and ascorbic acid.

In another preferred embodiment, the disorder is a vitamin B deficiency and the physiologically active substance employed in the treatment is selected from the group consisting of thiamine, riboflavin, pantothenic acid, pyridoxine, biotin, folic acid cyanocobalamin, hydroxocobalamin, methylcobalamin and salts and mixtures thereof.

In a particularly preferred embodiment, the disorder is a vitamin B12 deficiency and the physiologically active substance employed in the treatment is selected from the group consisting of cyanocobalamin, hydroxocobalamin and methylcobalamin.

In another preferred embodiment, the disorder is a vitamin B6 deficiency and the physiologically active substance employed in the treatment is pyridoxine (vitamin B6).

In another preferred embodiment, the disorder is a vitamin B9 deficiency and the physiologically active substance employed in the treatment s folic acid (vitamin B9).

In another embodiment, the disorder is an endocrine disorder and the water soluble physiologically active substance is a water soluble peptide or protein. The endocrine disorder may be selected from the group consisting of Acromegaly, Addison's Disease, Adrenal Cancer, Adrenal Disorder, Anaplastic Thyroid Cancer, Cushing's Syndrome, De Quatrain's Thyroiditis, Diabetes, Follicular Thyroid Cancer, Gestational Diabetes, Goiters, Graves' Disease, Growth Disorders, Growth Hormone Deficiency, Hashimoto's Thyroiditis, Hurthle Cell Thyroid Cancer, Hyperglycemia, Hyperparathyroidism, Hyperthyroidism, Hypoglycemia, Hypoparathyroidism, Hypothyroidism, Low Testosterone, Medullary Thyroid Cancer, MEN 1, MEN 2A, MEN 2B, Menopause, Metabolic Syndrome, Obesity, Osteoporosis, Papillary Thyroid Cancer, Parathyroid Diseases, Pheochromocytoma, Pituitary Disorders, Pituitary Tumors, Polycystic Ovary Syndrome, Prediabetes, Reproduction, Silent Thyroiditis, Thyroid Cancer, Thyroid Diseases, Thyroid Nodules, Thyroiditis, Turner Syndrome, Type 1 Diabetes, Type 2 Diabetes.

In a fourth aspect, the present invention relates to a kit comprising:
  at least one container comprising an aqueous composition comprising:
    0.001-25 wt. % of one or more fully dissolved physiologically active substances, the physiologically active substances having a water solubility in demineralized water of at least 15 mg/mL at 20° C.; wherein the one or more physiologically active substances are present in the aqueous composition in a concentration that is below their water-solubility limit at 20° C.;
    0.01-10 wt. % nicotinamide; and
    at least 60 wt. % water; and
  a nasal applicator device for intranasal administration in fluid communication with the aqueous composition;
wherein the nasal applicator device is adapted to provide a metered dose of 0.01 to 0.3 mL of the aqueous composition into the nasal cavity of a subject in the form of a spray or an aerosol, said metered dose providing 10-10,000 μg of the one or more physiologically active substances.

The kit provides a simple, user friendly way to administer the composition as defined herein.

In a preferred embodiment, the nasal applicator device is connected to the container comprising the composition.

In another preferred embodiment, the nasal applicator device is detachably connected to the container comprising the composition. The container can be removed from the nasal applicator device by, for example, unscrewing or unclipping. In this way, when the container is empty, a user may attach the nasal applicator device to a new, full container, thus avoid unnecessary wastage of the nasal applicator device.

The container may be a vial, ampule, bottle or other suitable receptacle for containing the composition. The container may have receiving means adapted to receive the nasal applicator device so that when the container is suitably connected to the nasal applicator device, the composition can be administered intranasally to a subject. The container may comprise means for opening the container such as a screw cap, snap line in the case of ampules, puncture seal or other such means for opening the container so that the composition can be transferred from the container to the nasal applicator device. In this way, the nasal applicator device can be refilled allowing the user to reuse the device rather than throwing the nasal applicator away after a single use.

In a fifth aspect, the present invention relates to the use of nicotinamide as an enhancer of intranasal absorption of a water soluble physiologically active substance having a water solubility in demineralized water of at least 15 mg/mL at 20° C. from aqueous solution from aqueous solution, wherein the aqueous solution further comprises 0.01-10 wt. % nicotinamide.

The present invention has been described above with reference to a number of exemplary embodiments. Modifications and alternative implementations of some parts or elements are possible, and are included in the scope of protection as defined in the appended claims.

EXAMPLES

Aqueous compositions comprising nicotinamide and a water soluble physiologically active substance in the amounts as described below in Examples 1-6 were prepared, and administered intranasally to a human subject, the compositions having the following general formulation:
water soluble physiologically active substance: 0.040-10 wt. %
nicotinamide: 3.5-10 wt. %
Phosphate buffer at pH 6.2 (+/−0.2): 0.10 wt. %
Benzalkonium chloride (preservative): 0.02 wt. %
Sodium chloride for isotonicity adjustment: q.s.
aqua purificata: ad 100%
Control compositions were prepared in which no nicotinamide was present.

Blood was taken prior to administration of the water soluble physiologically active substance and then at 30 and/or 60 minutes after administration. All blood plasmas analysed were obtained from whole blood by centrifugation at 1000 G for 10 minutes.

Example 1 (Vitamin B6)

1 mL of composition comprising 15 mg of pyridoxine phosphate (molecular weight 169; log P −0.77) and 35 mg nicotinamide was prepared. 0.1 mL of this aqueous composition was administered via a nasal spray to the nasal cavities of human subjects. As a control a 15 mg pyridoxine phosphate aqueous composition was used.

The blood plasma concentrations of vitamin B6/pyridoxine were determined after 0 and 60 minutes by HPLC analysis.

HPLC Instrumentation and Assay Procedure: LKB HPLC pump (Model 2150 with titanium parts) fitted with an inert injector (LKB Model 2154-002) and a 500-uL sample loop was used. A 4.6×250 mm LKB analytical column packed with 5-pm particles of reversed-phase material (TSK ODS-120T) was used in conjunction with a 3-cm guard column containing similar packing material (either LKB Spherisorb guard or Lichrosorb RP18). The eluent was 75 mmol/L $NaH_2PO_4$ buffer containing 75 mmol of $NaClO_4$, 8.5 mL of acetonitrile, and 0.5 mL of triethanolamine per liter and adjusted to pH 3.38 with concentrated $NaClO_4$. The flow rate was 1.2 mL/min, at a constant pressure of 12000 kPa. For postcolumn derivatization of pyridoxal phosphate with bisulfite ions as suggested by Coburn S F, Mahuren J D. A versatile cation-exchange procedure for measuring the seven major forms of vitamin B6 in biological samples. Anal Biochem, 1983, 129, 310-7. A Braun syringe pump was used connected to a T-junction and reaction coil. The postcolumn reagent consisted of $Na_2HPO_4$ buffer (250 mmol/L, pH 11.7) containing 1 g of sodium metabisulfite per liter. The flow rate of the postcolumn reagent was kept at 6 ml/h. Column effluents were monitored with a Model L5-20 fluorimeter (Perkin-Elmer Ltd., Beaconsfield, Bucks. HP9 1QA, U.K.) equipped with a 50-pL capillary flow cell. Excitation and emission wavelengths were set at 325 and 400 nm, respectively. The injection volume was 100 pL.

The results are shown in Tables 1 and 2.

TABLE 1

| invention: pyridoxine phosphate (1.5 wt. %) + nicotinamide (3.5 wt. %) | | | |
|---|---|---|---|
| Concentration pyridoxine phosphate (nmol/L) | | | |
| | t = 0 min. | t = 60 min. | Increase |
| 1 | 82 | 100 | 18 |
| 2 | 76 | 95 | 19 |
| 3 | 67 | 81 | 14 |
| | Average increase | | 17 |

TABLE 2

| control: pyridoxine phosphate - 1.5 mg (1.5 wt. %) | | | |
|---|---|---|---|
| Concentration pyridoxine phosphate (nmol/L) | | | |
| | t = 0 min. | t = 60 min. | Increase |
| 1 | 69 | 79 | 10 |
| 2 | 72 | 80 | 8 |
| 3 | 93 | 108 | 15 |
| | Average increase | | 11 |

Example 2 (Vitamin B9)

1 mL of a composition comprising 4 mg of folic acid (vitamin B9; molecular weight 441; log P −0.02) and 35 mg nicotinamide was prepared. 0.1 mL of this aqueous composition was administered via a nasal spray to the nasal cavities of human subjects. As a control a 4 mg folic acid aqueous composition was used.

An electrochemiluminescence immuno assay (Access Folate assay, Beckman Coulter, Inc—a competitive-binding receptor assay) was used to quantify the folate present in blood samples. Briefly, a serum specimen was treated to release folate from endogenous binding proteins. After neutralization of the reaction mixture, folate-binding protein, mouse antifolate-binding protein, folic acid-alkaline phosphatase conjugate, and goat antimouse capture antibody coupled to paramagnetic particles were added to the reaction vessel. Folate in the sample competes with the folic acid-alkaline phosphatase conjugate for binding sites on a limited amount of folate-binding protein. Resulting complexes bind to the solid phase via mouse antifolate binding protein. After incubation in a reaction vessel, materials bound to the solid phase are held in a magnetic field, while unbound materials are washed away. The chemiluminescent substrate Lumi-Phos 530 is added to the vessel and light generated by the reaction is measured with a luminometer. The light production is inversely proportional to the concentration of folate in the sample. The amount of analyte in the sample is determined from a stored, multipoint calibration curve. The assay is standardized to the World Health Organization (WHO) International Standard 03/178. (Beckman Coulter Assay Manual 2011, Beckman Coulter Inc., Fullerton, Calif.). The instrument used is a Beckman Coulter DXI 800.

TABLE 3 invention: folic acid (0.4 wt. %) + nicotinamide (3.5 wt. %)

Concentration folic acid (nmol/L)

| | t = 0 min. | t = 60 min. | Increase |
|---|---|---|---|
| 1 | 20.2 | 23.4 | 3.2 |
| 2 | 18.2 | 22.1 | 3.9 |
| 3 | 19.2 | 22.7 | 3.5 |
| | Average increase | | 3.5 |

TABLE 4 control: folic acid (0.4 wt. %)

Concentration folic acid (nmol/L)

| | t = 0 min. | t = 60 min. | Increase |
|---|---|---|---|
| 1 | 19.4 | 21.5 | 2.1 |
| 2 | 20.2 | 21.9 | 1.7 |
| 3 | 23.3 | 25.2 | 1.9 |
| | Average increase | | 1.9 |

Example 3 (Vitamin B12—Hydroxocobalmin 500 µg Dose)

1 mL of a composition comprising 5 mg of hydroxocobalmin (molecular weight 1346; log P −0.9) and 50 mg nicotinamide was prepared. 0.1 mL of this aqueous composition was administered via a nasal spray to the nasal cavities of human subjects. As a control a 0.5 mg of hydroxocobalmin aqueous composition was used.

An immuno assay (Access Vitamin B12 assay, Beckman Coulter Inc.) was used to quantify the folate present in blood samples. Briefly, a sample was added to a reaction vessel along with alkaline potassium cyanide and dithiothreitol. This treatment denatures B12 binding proteins and converts all forms of vitamin B12 to the cyanocobalamin form. After neutralization, intrinsic factor-alkaline phosphatase conjugate and paramagnetic particles coated with goat-antimouse IgG:mouse monoclonal anti-intrinsic factor were added to the sample. Vitamin B12 in the sample binds to the intrinsic factor conjugate, preventing the conjugate from binding to the solid phase anti-intrinsic factor. After incubation in a reaction vessel, materials bound to the solid phase were held in a magnetic field, while unbound materials were washed away. The chemiluminescent substrate Lumi-Phos 530 was added to the vessel and light generated by the reaction is measured with a luminometer. The light production is inversely proportional to the concentration of vitamin B12 in the sample. The amount of analyte in the sample was determined by means of a stored, multipoint calibration curve. (Instruction manual: Beckman Coulter Assay Manual 2015, Beckman Coulter Inc, Brea, Calif.).

TABLE 5 invention: B12 (0.5 wt. %) + nicotinamide (5 wt. %)

Concentration hydroxocobalmin (pmol/L)

| | t = 0 min. | t = 60 min. | |
|---|---|---|---|
| 1 | 442 | 957 | 515 |
| 2 | 371 | 636 | 265 |
| 3 | 539 | 1436 | 897 |
| | Average increase | | 559 |

TABLE 6 control: B12 (0.5 wt. %)

Concentration hydroxocobalmin (pmol/L)

| | t = 0 min. | t = 60 min. | Increase |
|---|---|---|---|
| 1 | 215 | 559 | 344 |
| 2 | 259 | 467 | 208 |
| 3 | 270 | 546 | 276 |
| | Average increase | | 276 |

Example 4 (Vitamin B12—Hydroxocobalmin, 75 µg Dose)

1 mL of a composition comprising 750 µg of hydroxocobalmin (molecular weight 1346; log P −0.9) and 50 mg nicotinamide was prepared. 0.1 mL of this aqueous composition was administered via a nasal spray to the nasal cavities of human subjects. As a control a 750 of hydroxocobalmin aqueous composition was used. The same method as in Example 3 was used for quantifying the hydroxocobalmin.

An immuno assay (Access Vitamin B12 assay, Beckman Coulter Inc.) was used to quantify the folate present in blood samples. Briefly, a sample was added to a reaction vessel along with alkaline potassium cyanide and dithiothreitol. This treatment denatures B12 binding proteins and converts all forms of vitamin B12 to the cyanocobalamin form. After neutralization, intrinsic factor-alkaline phosphatase conjugate and paramagnetic particles coated with goat-antimouse IgG:mouse monoclonal anti-intrinsic factor were added to the sample. Vitamin B12 in the sample binds to the intrinsic factor conjugate, preventing the conjugate from binding to the solid phase anti-intrinsic factor. After incubation in a reaction vessel, materials bound to the solid phase were held in a magnetic field, while unbound materials were washed away. The chemiluminescent substrate Lumi-Phos 530 is added to the vessel and light generated by the reaction is measured with a luminometer. The light production is inversely proportional to the concentration of vitamin B12 in the sample. The amount of analyte in the sample is determined by means of a stored, multipoint calibration curve. (Instruction manual: Beckman Coulter Assay Manual 2015, Beckman Coulter Inc, Brea, Calif.).

TABLE 7 invention: B12 (0.075 wt. %) + nicotinamide (5 wt. %)

Concentration hydroxocobalmin (pmol/L)

| | t = 0 min. | t = 60 min. | Increase |
|---|---|---|---|
| 1 | 291 | 408 | 117 |
| 2 | 321 | 328 | 7 |

TABLE 7-continued invention: B12 (0.075 wt. %) + nicotinamide (5 wt. %)

Concentration hydroxocobalmin (pmol/L)

|   | t = 0 min. | t = 60 min. | Increase |
|---|---|---|---|
| 3 | 349 | 437 | 88 |
| Average increase | | | 71 |

TABLE 8 control: B12 (0.075 wt. %)

Concentration hydroxocobalmin (pmol/L)

|   | t = 0 min. | t = 60 min. | Increase |
|---|---|---|---|
| 1 | 241 | 290 | 49 |
| 2 | 424 | 443 | 19 |
| 3 | 215 | 257 | 42 |
| Average increase | | | 37 |

Example 5 (Rh-Erythropoietin 0.040 wt. %)

1 mL of a composition comprising 400 µg rh-Erythropoietin (molecular weight 34000; log P 0) and 50 mg nicotinamide was prepared. 0.1 mL of this aqueous composition was administered via a nasal spray to the nasal cavities of human subjects. As a control a composition comprising 400 µg rh-Erythropoietin was used.

An immunoassay (Access erythropoietin (EPO), Beckman Coultier Inc.) was used to quantify the erythropoietin. Briefly, testing was performed on the Beckman Coulter DxI 800 (Beckman Coulter Inc.). Briefly, a sample was added to a reaction vessel along with the paramagnetic particles coated with mouse monoclonal anti-EPO, blocking reagent and the alkaline phosphatase conjugate. After incubation in a reaction vessel, materials bound to the solid phase were held in a magnetic field while unbound materials were washed away. Then, the chemiluminescent substrate Lumi-Phos 530 was added to the vessel and light generated by the reaction is measured with a luminometer. The light production is directly proportional to the concentration of EPO in the sample. The amount of analyte in the sample was determined from a stored, multi-point calibration curve. (Instruction manual: Beckman Coulter Access EPO, Beckman Coulter Access Immunoassay Systems, Beckman Coulter, Inc, Fullerton Calif. 2009).

TABLE 9 invention: Erythropoietin (0.04 wt. %) + nicotinamide (5 wt. %)

Concentration Erythropoietin (pmol/L)

|   | t = 0 min. | t = 60 min. | Increase |
|---|---|---|---|
| 1 | 9 | 11 | 2 |
| 2 | 13 | 16 | 3 |
| 3 | 10 | 14 | 4 |
| Average increase | | | 3 |

TABLE 10 control: Erythropoietin (0.04 wt. %)

Concentration Erythropoietin (pmol/L)

|   | t = 0 min. | t = 60 min. | Increase |
|---|---|---|---|
| 1 | 13 | 15 | 2 |
| 2 | 10 | 11 | 1 |
| 3 | 9 | 9 | 0 |
| Average increase | | | 1 |

Example 6 (Caffeine)

1 mL of a composition comprising 12.5 mg of caffeine (molecular weight 194; log P −0.79) and 50 mg nicotinamide was prepared. 0.2 mL of this aqueous composition was administered four times via a nasal spray to the nasal cavities of human subjects. As a control a 12.5 mg/ml of caffeine aqueous composition was used.

An HPLC separation method using a $C_{18}$ reverse phase column and 1% glacial acetic acid:methanol (83:17 V/V) as mobile phase was developed according to Pickard C. E., Stewart A. D., Hartley R. and Lucock M. D., A rapid HPLC method for monitoring plasma levels of caffeine and theophylline using solid phase extraction columns, Ann. Clin. Biochem., 1986, 23, 440-446. Conditions for chromatography were 0.5 ml/min solvent flow, injection volume 5 microL, run-time 20 minutes and UV detection at 274.4 nm. The UV detection was accompanied by MS detection for peak identification based on compound mass. Caffeine and the internal standard, 4-aminoantipyrine, were dissolved in artificial plasma as described in Alvi S. N, Muhammad M., Hammami M., Validated HPLC Method for Determination of Caffeine Level in Human Plasma using Synthetic Plasma: Application to Bioavailability Studies, J Chromatogr Sci, 2011, 49 (4), 292-296. The artificial plasma consisted of sodium chloride (145 mM), potassium chloride (4.5 mM), calcium chloride (32.5 mM), magnesium chloride (0.8 mM), urea (2.5 mM) and glucose (4.7 mM). Retention times were determined for caffeine, 4-aminoantipyrine, as well as for degradation products theobromine and theophylline to optimize separation of peaks. Subsequently, a dilution range of caffeine in artificial plasma was prepared in the range of 0.05-43.6 microgram/ml caffeine (final concentrations), with addition of internal standard at either 2.8 or 5.3 microgram/ml (final concentrations). Blood plasma samples were frozen at −20° C. upon delivery; the samples were thawed and gently shaken to mix the solution before sampling. Internal standard at 5.3 microgram/ml (final concentration) was added to 100 microliters of blood plasma. The sample was vortexed and centrifuged 5 minutes, and analysed after direct injection.

TABLE 11 invention: caffeine (10 mg) + nicotinamide (10 mg)

Concentration caffeine (mg/mL)

|   | t = 0 min. | t = 60 min. | Increase |
|---|---|---|---|
| 1 | 2887 | 3010 | 123 |
| 2 | 42 | 182 | 140 |
| 3 | 172 | 333 | 161 |
| Average increase | | | 141 |

TABLE 12

| | control: caffeine (10 mg) | |
|---|---|---|
| | Concentration caffeine (mg/L) | |
| t = 0 min. | t = 60 min. | Increase |
| 1 | 0 | 56 | 56 |
| 2 | 183 | 240 | 57 |
| 3 | 1280 | 1324 | 44 |
| | Average increase | | 52 |

For each of examples 1-6 the effect of nicotinamide on the blood level of the tested water soluble physiologically active substances was determined by calculating the percentage increase in absorption using the average increases. The results are summarized in table 13.

TABLE 13

| Increase in absorption of water soluble physiologically active substance relative to control | |
|---|---|
| Water soluble physiologically active substance | Increase in absorption relative to control (absence of nicotinamide) |
| Hydroxocobalamin | 203% |
| Hydroxocobalamin | 192% |
| Folic acid | 184% |
| Pyridoxine | 154% |
| Caffeine | 271% |
| Erythropoietin | 300% |

What is claimed is:

1. A method for administering water soluble physiologically active substances, the method comprising intranasally administering to a subject an aqueous composition comprising:
   (a) 0.001-25 wt. % one or more fully dissolved physiologically active substances comprising one or more vitamins selected from the group consisting of ascorbic acid, thiamine, riboflavin, pantothenic acid, pyridoxine, biotin, folic acid and salts and mixtures thereof, wherein the physiologically active substances have a water solubility in demineralized water of at least 15 mg/mL at 20° C., wherein the aqueous composition does not comprise vitamin B12, and wherein the aqueous composition does not comprise both niacin and ascorbic acid;
   (b) 0.01-10 wt. % nicotinamide; and
   (c) at least 60 wt. % water.

2. The method according to claim 1, wherein the physiologically active substance is present in the aqueous composition in a concentration that is below its water-solubility limit at 20° C.

3. The method according to claim 1, wherein the aqueous composition comprises 0.001-20 wt. % of the one or more physiologically active substances.

4. The method according to claim 1, wherein the aqueous composition comprises 0.05-8 wt. % nicotinamide.

5. The method according to claim 4, wherein the aqueous composition comprises 0.1-7 wt. % nicotinamide.

6. The method according to claim 5, wherein the aqueous composition comprises 0.5-6 wt. % nicotinamide.

7. The method according to claim 6, wherein the aqueous composition comprises 1-5 wt. % nicotinamide.

8. The method according to claim 1, wherein vitamin is selected from the group consisting of ascorbic acid, thiamine, riboflavin, pantothenic acid, pyridoxine, and biotin.

9. The method according to claim 1, wherein the vitamin is pyridoxine (vitamin B6).

10. The method according to claim 1, wherein the vitamin is folic acid (vitamin B9).

11. The method according to claim 1, wherein the physiologically active substance has a water solubility in demineralized water of at least 20 mg/mL at 20° C.

12. The method according to claim 11, wherein the physiologically active substance has a water solubility in demineralized water of at least 33 mg/mL at 20° C.

13. The method according to claim 12, wherein the physiologically active substance has a water solubility in demineralized water of at least 66 mg/ml at 20° C.

14. The method according to claim 1, wherein the aqueous composition has a pH in the range of 4.5 to 6.5 and an osmolarity of between 200 and 500 mOsm/L.

15. The method according to claim 14, wherein the aqueous composition has an osmolarity of 260 and 380 mOsm/L.

16. The method according to claim 1, wherein the method comprises intranasally administering the composition in a single metered spray in a dose of 0.01 to 0.3 ml.

17. A method of treating a disorder, the method comprising intranasally administering an aqueous composition comprising:
   (a) 0.001-25 wt. % of one or more fully dissolved physiologically active substances having a water solubility in demineralized water of at least 15 mg/mL at 20° C., wherein the one or more physiologically active substances are selected from the group consisting of thiamine, riboflavin, pantothenic acid, pyridoxine, biotin, folic acid and salts and mixtures thereof and are present in the aqueous composition in a concentration that is below their water-solubility limit at 20° C.;
   (b) 0.01-10 wt. % nicotinamide; and
   (c) at least 60 wt. % water,
   wherein the aqueous composition does not comprise vitamin B12 and is intranasally administered as a spray or an aerosol in a dose of 0.01 to 0.3 ml to provide the one or more physiologically active substances in a dose of 10-10,000 μg.

18. The method of treatment according to claim 17, wherein the disorder is a vitamin B deficiency.

19. The method of treatment according to claim 17, wherein the aqueous composition comprises 0.05-8 wt. % nicotinamide.

20. The method of treatment according to claim 19, wherein the aqueous composition comprises 0.1-7 wt. % nicotinamide.

21. The method of treatment according to claim 20, wherein the aqueous composition comprises 0.5-6 wt. % nicotinamide.

22. The method of treatment according to claim 21, wherein the aqueous composition comprises 1-5 wt. % nicotinamide.

23. A method for administering water soluble physiologically active substances, the method comprising intranasally administering to a subject an 0.05-0.3 mL aqueous composition comprising:
   (a) 0.001-10 wt. % one or more fully dissolved physiologically active substances comprising one or more vitamin B12 components selected from cyanocobalamin, hydroxocobalamin and methylcobalamin, wherein the physiologically active substances have a water solubility in demineralized water of at least 15 mg/mL at 20° C., and wherein the aqueous composition does not comprise both niacin and ascorbic acid;

(b) 0.5-5 wt. % nicotinamide; and
(c) at least 60 wt. % water,
wherein the intranasal administration of the aqueous composition provides 50-10,000 µg of the vitamin B12 component.

24. A method of treating a disorder, the method comprising intranasally administering an aqueous composition comprising:
(a) 0.001-10 wt. % of one or more fully dissolved physiologically active substances comprising one or more vitamin B12 components selected from cyanocobalamin, hydroxocobalamin and methylcobalamin, wherein the physiologically active substances have a water solubility in demineralized water of at least 15 mg/mL at 20° C.;
(b) 0.5-5 wt. % nicotinamide; and
(c) at least 60 wt. % water,
wherein the aqueous composition is intranasally administered as a spray or an aerosol in a dose of 0.05 to 0.3 mL to provide the vitamin B12 component in a dose of 50-10,000 µg.

\* \* \* \* \*